United States Patent [19]

McNeill et al.

[11] Patent Number: 5,342,624
[45] Date of Patent: Aug. 30, 1994

[54] DISPENSING DEVICE

[75] Inventors: Marion E. McNeill; Abdul Rashid; Howard N. E. Stevens, all of Glasgow, Scotland

[73] Assignee: British Technology Group Ltd., London, United Kingdom

[21] Appl. No.: 29,319

[22] Filed: Mar. 8, 1993

Related U.S. Application Data

[63] Continuation of Ser. No. 743,402, filed as PCT/GB90/00248, Feb. 15, 1990, abandoned.

[30] Foreign Application Priority Data

Feb. 16, 1989 [GB] United Kingdom ............ 8903566.1
Sep. 19, 1989 [GB] United Kingdom ............ 8921155.1

[51] Int. Cl.⁵ .................................................. A61K 9/48
[52] U.S. Cl. ................................... 424/451; 424/453; 424/454; 424/463; 424/422
[58] Field of Search ............... 424/463, 451, 453, 454, 424/456, 473, 422

[56] References Cited

U.S. PATENT DOCUMENTS

| | | | |
|---|---|---|---|
| 3,259,609 | 7/1966 | Satake et al. | 260/88.2 |
| 3,280,549 | 10/1966 | Hsu | 60/1 |
| 3,451,926 | 3/1967 | Haas | 210/59 |
| 3,745,659 | 7/1973 | Hsu | 33/127.7 R |
| 3,796,217 | 3/1974 | Arlen | 128/260 |
| 3,924,622 | 12/1975 | Brooke | 128/260 |
| 3,951,812 | 4/1976 | Hsu | 210/282 |
| 3,952,741 | 4/1976 | Baker | 128/260 |
| 3,953,406 | 4/1976 | Marsh, Jr. | 260/7.5 M |
| 3,975,350 | 8/1976 | Hudgin et al. | 260/30.4 N |
| 4,053,398 | 10/1977 | Venema | 210/41 |
| 4,138,013 | 2/1979 | Okajima | 424/453 |
| 4,150,108 | 4/1979 | Graham | 424/22 |
| 4,207,890 | 6/1980 | Mamajek et al. | 128/223 |
| 4,221,779 | 9/1980 | Graham | 424/78 |
| 4,267,295 | 5/1981 | Gallop et al. | 526/264 |
| 4,340,491 | 7/1982 | Lee | 210/764 |
| 4,419,236 | 12/1983 | Hsu | 210/282 |
| 4,434,153 | 2/1984 | Urquhart et al. | 424/22 |
| 4,438,258 | 3/1984 | Graham | 528/361 |
| 4,528,365 | 7/1985 | Graham | 528/392 |
| 4,542,176 | 9/1985 | Graham | 524/543 |
| 4,584,188 | 4/1986 | Graham | 424/19 |
| 4,663,148 | 5/1987 | Eckenhoff et al. | 424/453 |
| 4,774,092 | 9/1988 | Hamilton | 424/453 |
| 4,814,182 | 3/1989 | Graham et al. | 424/484 |
| 4,822,618 | 4/1989 | Schweiger et al. | 424/453 |
| 4,882,166 | 11/1989 | Graham et al. | 424/462 |

(List continued on next page.)

FOREIGN PATENT DOCUMENTS

| | | | |
|---|---|---|---|
| 578374 | 8/1985 | Australia. | |
| 0000291 | 1/1979 | European Pat. Off. | |
| 121331 | 10/1984 | European Pat. Off. | |
| 132384 | 1/1985 | European Pat. Off. | |
| 0153825 | 12/1990 | European Pat. Off. | |
| 0086463 | 6/1980 | Japan | 424/453 |
| 0080318 | 5/1982 | Japan | 424/453 |

(List continued on next page.)

OTHER PUBLICATIONS

Hsieg, D. S. et al. "Zero-order controlled ..." J. Pharm Sci (1983) vol. 72 Part 1 pp. 17–22.

Good. W. R. et al. "Hydrogels and controlled ..." AICHE Symp Ser (1981), vol. 77, Part 206, pp. 42–51, equivalent to Chem Abr 95 49344).

Heller, J. et al. "Release of Norethindrone ..." AICHE Symp Ser (1981) vol. 77, Part 206, pp. 28–36 (equivalent to Chem Abr 95 67886).

Primary Examiner—Thurman K. Page
Assistant Examiner—Raj Bawa
Attorney, Agent, or Firm—Nixon & Vanderhye

[57] ABSTRACT

Novel devices for the controlled release of active materials especially pharmaceutical are formed from at least two interpenetrating pieces. The male piece is water swellable and swells to disengage the female piece. The female piece is preferably formed from a thermoplastic, e.g. LDPE or from a soluble material such as gelatin which is rendered impermeable by an external coating of a hydrophobic material such as PVC. The devices find particular application as oral dosage forms for use in man.

23 Claims, No Drawings

U.S. PATENT DOCUMENTS

| Number | Date | Inventor | Class |
|---|---|---|---|
| 4,894,238 | 1/1990 | Embry et al. | 424/486 |
| 4,898,733 | 2/1990 | DePrince et al. | 424/425 |
| 4,931,288 | 6/1990 | Embrey et al. | 424/486 |
| 4,973,304 | 11/1990 | Graham et al. | 604/48 |
| 5,017,382 | 5/1991 | Embrey et al. | 424/486 |
| 5,079,009 | 1/1992 | Embrey et al. | 424/486 |
| 5,096,896 | 3/1992 | Graham et al. | 514/157 |
| 5,147,646 | 9/1992 | Graham | 424/424 |

FOREIGN PATENT DOCUMENTS

| Number | Date | Country |
|---|---|---|
| WO86/00538 | 1/1986 | PCT Int'l Appl. |
| WO88/04923 | 7/1988 | PCT Int'l Appl. |
| WO91/02763 | 3/1991 | PCT Int'l Appl. |
| 436236 | 10/1935 | United Kingdom |
| 733987 | 7/1955 | United Kingdom |
| 943718 | 12/1961 | United Kingdom |
| 1035877 | 7/1966 | United Kingdom |
| 1118430 | 7/1968 | United Kingdom |
| 1135966 | 12/1968 | United Kingdom |
| 1204900 | 9/1970 | United Kingdom |
| 1308129 | 2/1973 | United Kingdom |
| 1318259 | 5/1973 | United Kingdom |
| 1346609 | 2/1974 | United Kingdom |
| 1377452 | 12/1974 | United Kingdom |
| 1445137 | 8/1976 | United Kingdom |
| 1486288 | 9/1977 | United Kingdom |
| 1489965 | 10/1977 | United Kingdom |
| 1494814 | 12/1977 | United Kingdom |
| 1551620 | 8/1979 | United Kingdom |
| 1556584 | 11/1979 | United Kingdom |
| 2020181 | 11/1979 | United Kingdom |
| 2047093B | 11/1979 | United Kingdom |
| 2046275A | 11/1980 | United Kingdom |
| 2047094 | 11/1980 | United Kingdom |
| 2086400B | 5/1982 | United Kingdom |
| 2090264 | 7/1982 | United Kingdom |
| 2094256 | 9/1982 | United Kingdom |
| 2099699 | 12/1982 | United Kingdom |
| 2108571 | 5/1983 | United Kingdom |
| 2178660 | 2/1987 | United Kingdom |
| 2189390B | 10/1987 | United Kingdom |
| 2206046B | 12/1988 | United Kingdom |
| 2206047 | 12/1988 | United Kingdom |
| 2252043 | 7/1992 | United Kingdom |
| WO92/13521 | 8/1992 | World Int. Prop. O. |

DISPENSING DEVICE

This is a continuation of application Ser. No. 07/743,402, filed Feb. 15, 1990, as PCT/GB90/00248, now abandoned.

This invention relates to novel devices for the controlled release of an active material especially a pharmaceutically active drug. More particularly this invention relates to devices which are adapted to administer the active material over a relatively short period following a delay after administration—a pulsed release device.

A wide variety of devices for the controlled release of drugs have been proposed. These dosage forms which may be termed "sustained release", "timed release", "prolonged release" or "controlled release" forms are designed to dispense the drug in a controlled reproducible manner. Previous attempts to provide a release in a short burst over a period of the order of minutes e.g. those described in U.S. Pat. No. 3,952,741 have not been successful in controlling the delay before which the pulsed release of active material occurs.

We have now discovered a novel device which provides a pulsed release of active material after a reproducible time delay wherein the active material is contained within a capsule formed from at least two interpenetrating pieces, one of which a male piece Is formed from a water swellable material which when wet swells and disengages the female piece.

Accordingly, from one aspect this invention provides a controlled release device which comprises a capsule containing active material, said capsule being formed from at least two interpenetrating pieces, the male portion of which is formed from a water swellable material and swells so as to disengage the female piece upon exposure to an aqueous medium.

In a preferred embodiment the device comprises a capsule having at least one orifice extending through the wall of the capsule which orifice is closed by a water swellable plug such that upon immersion in an aqueous medium said plug swells and separates from the capsule.

Surprisingly we have discovered that provided the male piece is of such material and of such dimensions that its swelling does result in its ejection from the orifice in the capsule wall that ejection takes place after a reproducible time interval following the exposure of the device to an aqueous medium. Thereafter the contents of the capsule are released into the surrounding medium. The devices are advantageous particularly as oral dosage forms for use in man since they enable the maximum quantity of active material to be incorporated into a capsule of any given size.

Where the device is intended for use as an oral dosage form the male piece (the plug) may be constructed from any water swellable material which is biologically and medically compatible, non-allergenic, insoluble in and non irritating to body fluids and tissues. The water swellable material is preferably a hydrogel.

The choice of the material used to form the water swellable piece in any particular device will vary according to a number of parameters which affect the desired delay following immersion in the aqueous medium before the contents are released. The rate of swelling and the degree of swelling of the material are important parameters in determining the delay obtained from a particular device. The material should always be such that when formed into a male piece of appropriate dimensions for use in a particular device it will maintain a substantially water-tight fit between the male and female portions throughout the delay period. For any given piece the time delay before the plug is ejected from the orifice is inversely proportional to the rate of swelling of the material from which it is constructed.

The dimensions of the plug may also be used to vary the delay time. In particular that delay is proportional to the length of that part of the male piece which lies within the jaws defining the orifice of the female piece, i.e. in the preferred embodiment the length of the plug within the orifice.

The position of the plug within the orifice may also be utilised to regulate the delay before the plug is ejected. In particular where the outer surface of the plug is recessed so as to lie below the level of the mouth of the orifice the ejection of the plug will be delayed by a time which is a function of the depth of the recess. In a preferred embodiment the devices of this invention comprise a retaining means situated on the interior face of the orifice. The means which may conveniently comprise a ridge or ledge limit which engages the plug and limits the depth to which it can be inserted into the orifice.

From the foregoing it will be appreciated that for any particular device of this invention the delay time after immersion in an aqueous medium until the plug is ejected may be varied by the empirical adjustment of one or more of the above parameters. The delay time may vary over a wide interval say anything from 0.5 hours to 12 hours according to the application but may extend over much greater intervals e.g. up to 7 or even 14 days or longer in applications where such lengthy delays are advantageous. In a preferred embodiment the device will be constructed in such a way that the plug is ejected whilst the inner surface thereof remains dry, i.e. before any significant quantity of water enters the capsule. Such devices will be constructed so as to ensure that the plug maintains a water-tight seal within the orifice and that no significant quantity of water permeates through the plug prior to its ejection.

Again, where the device is intended for use as an oral dosage form the walls of the female piece of the capsule may be formed from any material which is biologically and medically compatible with, non allergenic and insoluble in and non-irritating to body fluids and tissues. The walls may be formed from a biodegradable material provided that the material retains its structural integrity for at least the length of the delay time. The walls of the female piece of the capsule are preferably constructed so as to be impermeable to the passage of water. Where water permeable materials are employed the device should be preferably constructed so as to avoid the permeation of any significant quantity of water into the interior of the capsule prior to the ejection of the plug from the orifice.

The walls of the female piece are preferably constructed from a material which is not water swellable. Where the walls of the capsules are not of uniform construction, that portion of them which define the jaws of the orifice will preferably be constructed from material which is not water swellable. Where any portion of the female piece and in particular that which defines the jaws of the orifice is constructed from a water swellable material, the preferred materials possess a lower rate and a lower degree of swelling than that used to form the male piece. The device will preferably be designed so as to ensure that the joint between the male and female piece remains water-tight. The walls of the capsule will be constructed so as to ensure that they retain their structural integrity at least until the capsule separates into two pieces.

The capsule may be formed in any convenient shape, for example spheroidal, ellipsoidal or cylindrical. Capsules which are generally cylindrical are preferred. A preferred form of the device of the present invention comprises a hollow cylinder open at one or both ends, having a plug of water swellable material in the open end or ends. Such devices may be readily formed, e.g. from an extruded plastic tube cut into lengths and optionally sealed at one end and closed at the open end or ends by the insertion of a plug or plugs. Alternatively the capsule may be formed by forming a cylinder around a rod; by coating a solution of polymer or organosol onto a former; by compression or injection moulding of a suitable thermoplastic polymer; by powder compression or by direct reaction moulding.

The plug may be inserted so that its top is flush with the end face of the tube or may be inserted to a greater depth so that the walls of the cylinder extend beyond the outer surface of the plug. The length of the plug and the depth of its insertion will be predetermined so as to control the delay prior to the ejection of the plug. The plug is conveniently cylindrical in shape and such shapes may be readily cut from a rod of material. The plug may adopt other geometries such as cone sections. The ratio of the length of these cylindrical plugs to their diameter is preferably in the range 0.1:1 to 20:1 and more preferably in the range 0.2:1 to 2:1.

The cylindrical devices are conveniently of a size which may be swallowed and hence they find use as oral dosage forms for man in particular, but also in animals. Typically the length of the hollow cylinder will be in the range 5 to 100 mm, preferably 10 to 30 mm and the external diameter will be in the range 1 mm to 20 mm. Typically the devices will have external dimensions corresponding to those of known oral dosage forms, e.g. capsules having sizes in the range triple zero to zero and from 1 to 8. The length of the plug will preferably be from 1 to 5 mm. The plug may preferably be recessed to a depth of not more than 5 mm and preferably not more than 2 mm. In another embodiment the devices of this invention may be significantly smaller so as to facilitate the inclusion of a plurality of devices in a single dosage form, e.g. a capsule. This enables different release patterns to be obtained.

The contents of the device may take the form of the active material as such, e.g. as a particulate solid or may take the form of any other convenient dosage form. For example, the active material may be combined with a conventional excipient and be introduced into the device as a powder or as a fluid solution or suspension (provided that the fluid medium does not interact significantly with the materials used to form the wall of the capsule) or take the form of compressed tablets of excipient and carrier. Either a single tablet or a plurality of such tablets may be introduced. A further alternative is to introduce the active material in a modified dosage form, e.g. a coated material such as is described in British Patent 2112730. This enables the release profile of the device to be modified, e.g. where a particulate active material is employed it will be released as a pulse of active material, whereas where a modified dosage form is employed that form may be released into the environment after the pre-determined delay and the subsequent release profile will be that of the modified dosage form. A combination of these alternatives may be employed.

The devices of this invention find wide application in medical, including veterinary, contexts and in horticulture and agriculture as well as outside these areas.

Specific classes of drug which may be utilised as the active material in a pulsed release device of this invention include hypnotics, sedatives, tranquilisers, antipyretics, anti-inflammatory agents, anti-histamines, anti-tussives, anti-convulsants, anti-asthmatics, muscle relaxants, anti-tumour agents, for example those for the treatment of malignant neoplasia, local anaesthetics, anti-Parkinson agents, topical or dermatological agents, diuretics, for example those containing potassium, such as potassium iodide, preparations for the treatment of mental illness, for example preparations containing lithium for use in the treatment of manic depression or containing prostaglandins for the treatment of schizophrenia, anti-spasmodics, anti-ulcer agents, $\beta$ blockers such as atenolol and metoprolol ; calcium antagonists such as nifedipine and nitrendpine, ACE inhibitors such as enalapril and captopril, $\beta_2$ agonists such as salbutamol and terbutaline, preparations containing various substances for the treatment of infection by pathogens including anti-fungal agents, for example metronidazole, anti-parasitic agents and other anti-microbials, anti-malarials, cardiovascular agents, preparations containing hormones, for example androgenic, estrogenic and progestational hormones, notably steroids such as oestradiol, sympathomimetic agents, hypoglycaemic agents, contraceptives, nutritional agents, peptides and proteins, nitrates such as isorbide dinitrate, mononitrate and GTN; xanthines such as theophyiline; NSAID's such as piroxicam and diclofenac; benzodiazepines such as triazolam and zopiclone; $\alpha$ blockers such as prazosine and alfuzosine; antivirals such as acyclovir, zidovudine and ampligen, cephalosporins such as cefaclor, antispasmodics such as alverine and salicylates such as 5 amino salicylic acid; preparations containing enzymes of various types of activity, for example chymotrypsin, preparations containing analgesics, for example aspirin, and agents with many other types of action including nematocides and other agents of veterinary application. Mixtures of active substances may be incorporated into the controlled release device.

The controlled release devices of this invention are also useful in the treatment of diabetes and pernicious anaemia where, for example, the controlled release of insulin and cobalamin, respectively, may be utilised.

Moreover, the release devices of this invention are suited to treatment, both prophylactic and therapeutic, of tropical diseases; for example malaria, leprosy, schistosomiasis and clonorchiasis. Examples of drugs which can be used as biologically active substance in release devices of this invention for the treatment of these and other tropical diseases include quinine, sulphonamides, rifamycin, clofazimine, thiambutasine, chlorphenyl derivatives, chlorguamide, cycloguanil, pyrimethamine, sulphadiazine, trimethoprim, quinoline derivatives such as pamaquine, chloroquine, pentaquine, primaquine and amodiquine, pararosaniline, sulphamethizole, quinacrine, dapsone, sodium sulphoxone, sulphetrone, sodium hydnocarpate and sodium chaulmoograte. Drugs of particular effectiveness are cycloguanil, pyrimethamine and sulphadiazine.

The release devices of this invention are also very well suited to veterinary applications. Examples include preparations of antibiotics for general antibacterial activity and also in the treatment of anaplasmosis in cattle; preparations for provision of a wide spectrum of activity against both ectoparasites, for example termites and endoparasites including anthropods, arrested larvae stages of nematodes, lungworms and general strongyles: these may comprise avermectins; preparations for provision of activity against tremotode, cestode and roundworm infections: these may comprise amoscanate and praziquantel: preparations for provision of activity against theileria in cattle: these may comprise biologically active naphthoquinones such as menoctone; preparations for provision of activity against babesiosis in cattle, horses and dogs: these may comprise berenil, amidocarb and diampron; preparation for provision of activity against liver fluke in sheep and cattle and against Haemonchus species: these may comprise closantel.

The devices of the present invention may also be combined with another dosage form which will combine the release profile of the novel devices with that of the other dosage form. Thus, for example, two separate devices according to this invention may be joined end to end so that the active materials are separated by a wall. Alternatively, two separate female pieces may be closed by a single male piece or plug. For example, two separate cylindrical pieces may be mounted upon opposite ends of a rod of water swellable material. By controlling the depth of penetration of the rod into each cylindrical piece it is possible to achieve either simultaneous or sequential release of the contents of the cylindrical pieces. Also a device according to this invention may be joined to or combined with another controlled release device (of appropriate dimensions).

A further preferred embodiment of this invention comprises devices coated with an enteric coating so as to pass through the stomach and release the active material in the intestine. Such devices can be designed so as to release the active at a set period after they pass out of the stomach. They may be designed to release in the colon. Examples of suitable enteric coating agents which may be employed include cellulose acetate phthalate, polyvinyl acetate phthalate, pH sensitive polyacrylate and polymethyacrylate derivatives and hydroxypropylmethyl cellulose phthalate.

A further preferred embodiment of this invention comprises those devices wherein the plug comprises an active substance which diffuses into an aqueous medium over a period of time. A particularly preferred embodiment are those devices wherein the plug is formed from a hydrogel comprising an active substance e.g. as described in our British Patents 2047093 and 2047094. Such devices provide a controlled release of an active material during the period prior to the expulsion of the plug (which release may persist after that time if so desired). It will thereby be appreciated that the devices of this invention can be designed to provide a variety of release profiles. They are characterised in that they release a sharp pulse of active material either as such and/or in a modified dosage form after a predetermined delay. This feature enables devices which provide pulsed or controlled release profiles or a combination of the two to be designed by combining these characteristic features e.g. with a drug loaded plug a sustained release of active may be obtained during the period of the delay. By combining one or more devices of the invention in a single dosage form a device may be prepared which combines these profiles or superimposes them to provide novel devices having improved release profiles.

The walls of the female portion of the capsule may be formed from a wide variety of materials. They may be of homogenous construction or they may be laminated. Examples of materials suitable for use in the construction of the walls include polyethylene, polypropylene, poly(methylmethacrylate), polyvinyl chloride, polystyrene, polyurethanes, polytetrafluoroethylene, nylons, polyformaldehydes, polyesters, cellulose acetate and nitrocellulose.

A preferred construction utilises an impermeable coating to cover the exterior of a capsule formed from a water soluble material. The coating may conveniently be formed by dipping a capsule in a solution of any of the above-mentioned materials so as to form a layer which is impermeable to water. The capsule may also be spray coated with solutions of the above materials in which use the exterior has an impermeable coating and the interior may be partially coated. A preferred class of capsules are the conventional hard gelatin or starch capsules coated with a solution of polyvinyl chloride or a polyvinyl acetate copolymer or an ethyl cellulose solution (plasticised as necessary). A further preferred class of capsules are those which are coated with a film of a biodegradable polymer such as certain hydroxy butyric acid copolymers. Such devices are advantageous in that they are simple to construct and insofar as their soluble interiors dissolve In the aqueous medium leaving either a thin flexible coating to be eliminated from the body or a coating which can be degraded in the body.

The male piece (that is in the preferred embodiment the plug) used in the devices of this invention may be formed from a wide variety of water swellable materials. The suitability of a material for use in a particular device depends upon its degree of swellability, its rate of swelling when immersed in an aqueous medium, the permeability of the material and the relationship of these parameters to the dimensions of the device and the delay which is required before the plug is ejected. The suitability of a particular material may most readily be determined by empirical means.

A preferred class of hydrophilic materials from which the plugs may be constructed are hydrogels. Examples of suitable synthetic hydrogels which may be employed in the devices of this invention include poly(hydroxyethyl-methacrylate); poly(N-vinyl-pyrolidone), poly(acrylamide); poly(acrylic acid); poly(vinylalcohol) and poly(methacrylic acid). A particularly preferred class of hydrogels are those crosslinked hydrophilic polymers comprising polyethylene oxide residues, preferably those which contain crystalline regions and have a crystalline melting temperature (Tm) of $-10°$ C. to $+70°$ C. Chemical crosslinking may be effected in a manner known per se. Where the hydrophilic polymer comprises functional groups which comprise an active hydrogen atom; chemical crosslinking may be effected by means of a di- or poly-isocyanate [such as bis-(4-isocyanatophenyl)methane or bis-(4-isocyanatocyclohexyl methane] or a di- or poly-linear or cyclic olefinically unsaturated ether (such as acrolein tetramer); for example, as disclosed in our UK Patents 2047093, 2047094 and 2108517, from which it will be apparent that where a diisocyanate or di-olefinically unsaturated ether is used a reactant comprising at least three active hydrogen atoms must also be present to ensure chemical crosslinking.

Entanglement crosslinking may be utilised, especially where the hydrophilic polymer has a high (for example, $\overline{M}_n$ greater than 100,000) molecular weight, by chemically crosslinking, in intimate admixture with the hydrophilic polymer, at least one monomer of functionality greater than two. Examples of such monomer include di- and poly-olefinically unsaturated hydrocarbons, such as divinyl benzene, and di- and poly-olefinically unsaturated esters or ethers, such as acrolein tetramer, triallyl cyanurate or glycol dimethacrylate.

Preferred hydrophilic polymers comprising polyethylene oxide residues have a number average molecular weight, $\overline{M}_n$, of the polyethylene oxide greater than 1,500, preferably greater than 3,000; for example, from 4,000 to 12,000 or higher.

The hydrophilic polymer may be a homopolymer or a random, alternating or block copolymer, specially a homopolymer or a random or block copolymer of ethylene oxide with, for example, a homologue such as propylene oxide or oxetane.

The hydrophilic polymer, for example, polyethylene oxide, may also be foamed in a manner known per se. For example, the polyethylene oxide may be chemically crosslinked by means of a di- or poly-isocyanate in the presence of water; the polyethylene oxide may also be foamed by the direct injection of a pneumatogen, such as a fluorocarbon; for example, fluorotrichloromethane (e.g. "ARCTON" ex ICI Ltd: "ARCTON" is a registered Trademark.

The walls of the capsule may also be formed from such hydrogels. However, they will preferably not be constructed from the identical hydrogel as may be employed in the construction of the plug. They will preferably have a lower rate of swelling than that of the plug as this assists in maintaining a water-tight seal. The hydrogels are permeable to water and in this embodiment the devices may be constructed so as to permit the ingress of water into the interior of the capsule prior to the ejection of the plug.

The invention is illustrated by the following examples.

EXAMPLE 1

A series of devices were prepared comprising a cylindrical capsule wherein the open end is closed by a plug. The interior of capsule was charged with 9.6 mg of salbutamol sulphate. In all cases the capsule was closed with a plug of appropriate diameter and formed from a hydrogel produced by the batch polymerisation of 2.8 parts of Desmodur W [a proprietary bis-(4-isocyanato cyclohexyl)methane] with 1.2 parts of hexane triol and 1 part of a polyethylene glycol having Mn 8000 using ferric chloride as a catalyst. The release profile of each device was tested in water at 37° C. using a U.S. Pharmacopoeia dissolution bath. The quantity of drug released was monitored by u.v. spectroscopy. The time at which drug was released was noted.

The composition of the devices is summarised in the following table:

|  | (1) | (2) | (3) | (4) |
| --- | --- | --- | --- | --- |
| Capsule Material | PVC | PTFE | PVC | PTFE |
| Exterior Diameter | 8.0 mm | 6.45 mm | 6.0 mm | 6.45 mm |
| Interior Diameter | 5.94 mm | 4.75 mm | 2.9 mm | 4.75 mm |
| Plug Diameter | 6.2 mm | 5.0 mm | 3.0 mm | 4.82 mm |
| Plug Length | 4 mm | 4.82 mm | 3.0 mm | 4.0 mm |
| Recess Depth | 0 | 0 | 0 | 0 |
| Release Time | 12.5 hrs | 1.75 hrs | 8.5 hrs | 2.0 hrs |

| | (5) | (6) | (7) | (8) |
| --- | --- | --- | --- | --- |
| Capsule Material | PTFE | PTFE | PTFE | PTFE |
| Exterior Diameter | 6.45 mm | 6.45 mm | 6.45 mm | 6.45 mm |
| Interior Diameter | 4.75 mm | 4.75 mm | 2.84 mm | 2.84 mm |
| Plug Diameter | 4.8 mm | 4.8 mm | 3.0 mm | 3.0 mm |
| Plug Length | 5.0 mm | 5.0 mm | 4.0 mm | 5.0 mm |
| Recess Depth | 1.78 mm | 2.22 mm | 0 | 0 |
| Release Time | 5.5 hrs | 9.25 hrs | 4.75 hrs | 6.75 hrs |

EXAMPLE 2

A series of hydrogel cylinders were prepared by batch polymerising 5.5 parts of Desmodur W with 3 parts of hexane triol and 1 part of a polyethylene glycol having Mn 3830 using ferric chloride as the catalyst. The polymerisation was carried out in a suitable mould into which a former was inserted so as to form the hollow cylinders.

A series of hydrogel rods were prepared by batch polymerising 2.8 part of Desmodur W, 1.2 parts of hexane triol and 1 part of a polyethylene glycol having Mn 8000 using ferric chloride as the catalyst.

These rods were cut in appropriate lengths to form plugs which were inserted into an appropriately sized cylinder to form a device according to this invention. Each cylinder contained a quantity of salbutamol sulphate. The release profile of each device was tested in water at 37° C. using a U.S. Pharmacopoeia dissolution bath. The time at which the drug was released was noted.

The particulars of these devices and the results obtained are summarised in the following table:

| No. of Devices | 6 | 5 | 3* | 3* |
| --- | --- | --- | --- | --- |
| Capsule Length | 12 mm | 9 mm | 9 mm | 9 mm |
| Drug Weight | 50 mg | 25 mg | 10 mg | 10 mg |
| Plug Length | 3 mm | 3 mm | 3 mm | 3 mm |
| Plug Diameter | 3.25 mm | 3.25 mm | 3.4 mm | 3.4 mm |
| Plug Recission | 0.55 mm | 0.55 mm | 1 mm | 2 mm |
| Mean Release Time | 8.3 hrs | 5.8 hrs | 4.9 hrs | 10.8 hrs |

*Plug recession controlled by provision of a ridge on the interior of the capsule.

EXAMPLE 3

Two hydrogel rods of the same diameter were produced by polymerising (a) 1 part of polyethylene glycol (Mn 4000), 3 parts of hexane triol and 5.5 parts of Desmodur W and (b) 1 part of polyethylene glycol (Mn 4000), 2 parts hexane triol and 4 parts Desmodur W. The rods (a) and (b) exhibited different rates of swelling when immersed In water, (a) being low swelling and (b) moderately swelling. Sections of these rods were used as plugs in two identical capsules formed from a rigid thermoplastic which contained 10 mg of sulbutamol sulphate. The release profile of each device was measured using the technique described in the previous example.

The release times were:
(a) 5.3 hours and (b) 4.8 hours.

EXAMPLE 4

A series of capsules were made from hollow cylinders of various materials closed at one end and plugged with a hydrogel cylinder having the same composition as that employed in Example 1. The devices were charged with salbutamol sulphate and their release profile measured using the identical procedure to that of Example 1. The results were as follows:

| No. of Devices | 6 | 1 | 4 |
|---|---|---|---|
| Capsule Material | Rigid PVC | Flexible PVC (Wall thickness 0.025") | Semi Flexible PVC (Wall thickness 0.04") |
| Capsule Length | 17 mm | 18 mm | 18 mm |
| Capsule Internal Diameter | 5.33 mm | 6.1 mm | 5.3 mm |
| Plug Length | 5.0 mm | 3 mm | 5 mm |
| Plug Diameter | 5.45 mm | 6.35 mm | 5.6 mm |
| Plug Recission | 0 | 0 | 0 |
| Mean Release Time | 3.75 hrs | 2.75 hrs | 18.6 hrs |
| No. of Devices | 6 | 6 | |
| Capsule Material | LDPE* (Wall thickness 0.02") | PVC Coated gelatin+ | |
| Capsule Length | 17 mm | Gelatin capsule Size 1 | |
| Capsule Internal Diameter | 6.3 mm | | |
| Plug Length | 5 mm | 3.8 mm | |
| Plug Diameter | 6.5 mm | 6.45 mm | |
| Plug Recission | 0 | 0 | |
| Mean Release Time | 2.5 hrs | 5.1 hours | |

*LDPE is Low Density Polyethylene
+Gelatin capsule dip coated 18 times with a 5% solution of unplasticised PVC

EXAMPLE 5

Two series of cylindrical devices were prepared. All of these devices used LDPE capsule identical to that utilised in Example 4 except that the capsule length was 18 mm. The first series of three devices utilised a plug having a length of 5 mm and the second series of three devices a plug of length 7 mm. All the plugs were formed from a hydrogel having an identical composition to that utilised in Example 1. The release profiles of the six devices was determined in the manner reported in Example 1.

The mean release times were:
First series 3.3 hours
Second series 4.2 hours

EXAMPLE 6

Two devices were prepared identical to those utilised in the first series of Example 5 except that the plugs were recessed to a depth of 1 mm and 2 mm. The release times of those devices were 3.6 hours and 7.3 hours.

We claim:

1. A pulsed release device which comprises a capsule containing at least one active material, said capsule comprising a female piece and a plug interpenetrating said female piece and being disengageable from said female piece, said plug being formed from a water-swellable material which swells so as to disengage from said female piece upon exposure to an aqueous medium, said plug disengaging from said female piece after a time delay of at least about half an hour after exposure to said aqueous medium, said female piece being constructed so as to be impermeable to the passage of water, said active material being selected from the group consisting of medical, veterinary, horticultural and agricultural materials.

2. A device according to claim 1, wherein said female piece has at least one orifice extending through a wall thereof, said at least one orifice being closed by said plug.

3. A device according to claim 1, wherein said female piece is a cylindrical tube which is closed at one end and open at the other.

4. A device according to claim 1, wherein said female piece is a cylindrical tube which is open at both ends.

5. A device according to claim 1, wherein said plug comprises a cylindrical plug or plugs.

6. A device according to claim 5, wherein an outer surface of the plug lies flush with a wall of the capsule.

7. A device according to claim 6, wherein said outer surface of the plug is recessed and lies below the wall of the capsule.

8. A device according to claim 7, wherein said plug is recessed to a depth of not more than 5 mm.

9. A device according to claim 1, wherein the plug is formed from a hydrogel.

10. A device according to claim 9, wherein the hydrogel is derived from a homo- or co-poly(alkylene oxide) cross-linked by reaction with isocyanate or unsaturated cyclic ether groups.

11. A device according to claim 9, wherein said hydrogel comprises an active substance.

12. A device according to claim 1, wherein said female piece is formed from a water impermeable material.

13. A device according to claim 12, wherein said water impermeable material is selected from the group consisting of polyethylene, polypropylene, poly(methylmethacrylate), polyvinyl chloride, polystyrene, polyurethanes, polytrafluoroethylene, nylons, polyformaldehydes, polyesters, cellulose acetate and nitrocellulose.

14. A device according to claim 12, wherein said female piece is formed from a thermoplastic.

15. A device according to claim 12, wherein said water impermeable material is low density polyethylene.

16. A device according to claim 1, wherein said female piece is constructed from a water soluble material having its exterior surface covered with an impermeable coating.

17. A device according to claim 16, wherein said water soluble material is gelatin or starch.

18. A device according to claim 16, wherein said impermeable coating is polyvinyl chloride.

19. A device according to claim 1, wherein said active material is pharmaceutically active.

20. A device according to claim 19, wherein said active material is a particulate solid.

21. A device according to claim 19, wherein said active material is present in a modified dosage form.

22. A device according to claim 1, wherein the capsule has a length of from 10 to 30 mm and an external diameter of from 1 to 20 mm.

23. A device according to claim 22, wherein an external surface is provided with an enteric coating.

* * * * *